US006479262B1

(12) United States Patent
Delagrave

(10) Patent No.: US 6,479,262 B1
(45) Date of Patent: Nov. 12, 2002

(54) SOLID PHASE ENZYMATIC ASSEMBLY OF POLYNUCLEOTIDES

(75) Inventor: Simon Delagrave, Avondale, PA (US)

(73) Assignee: Hercules, Incorporated, Wilmington, DE (US)

( * ) Notice: Subject to any disclaimer, the term of this patent is extended or adjusted under 35 U.S.C. 154(b) by 0 days.

(21) Appl. No.: 09/571,774

(22) Filed: May 16, 2000

(51) Int. Cl.[7] ............ C12P 19/34; C12Q 1/68; C07H 21/00; C07H 21/02; C07H 21/04; C07H 19/04; G01N 33/566

(52) U.S. Cl. ......... 435/91.1; 435/6; 536/25.3; 536/25.31; 536/25.32; 536/25.33; 536/25.34; 536/24.3; 536/26.22; 436/501; 424/94.1

(58) Field of Search ............... 536/25.31, 25.3, 536/25.32, 25.33, 25.34, 26.22, 24.3, 421.3, 424.3; 435/6, 91.2, 91.1; 436/501; 424/94.1

(56) References Cited

U.S. PATENT DOCUMENTS

| | | | |
|---|---|---|---|
| 4,458,066 A | * 7/1984 | Caruthers et al. | 536/27 |
| 5,602,000 A | * 2/1997 | Hyman | 435/91.1 |
| 5,914,245 A | 6/1999 | Bylina et al. | 435/19 |
| 5,935,527 A | 8/1999 | Andrus et al. | 422/131 |
| 5,942,609 A | * 8/1999 | Hunkapiller et al. | 536/25.3 |

FOREIGN PATENT DOCUMENTS

| | | |
|---|---|---|
| DE | 43 43 591 A1 | 6/1995 |
| DE | 196 33 427 A1 | 3/1998 |
| DE | 198 12 103 A1 | 9/1999 |
| DE | 199 28 591 A1 | 12/1999 |
| EP | 0 406 937 | 1/1991 |
| EP | 1 149 905 A1 | 10/2001 |
| GB | 2 169 605 A | 7/1986 |
| WO | WO 83/02626 * | 8/1983 |
| WO | WO 90/00626 | 1/1990 |
| WO | WO 93/19202 | 9/1993 |
| WO | WO 94/14972 | 7/1994 |
| WO | WO 98/27230 | 6/1998 |
| WO | WO 99/14318 | 3/1999 |

OTHER PUBLICATIONS

Dietrich R. et al., "Gene assembly based on blunt–ended double–stranded DNA modules", Biotechnology Techniques, vol. 12, pp. 49–54 (Jan. 1998).*
English translation of pp. 2–11 from the German patent DE 19812103 A1.*
Wong et al. Enzymes in Organic Synthesis. J. Am. Chem. Soc., vol. 112, pp. 945–953.*
Isono et al. Purification and Reaction of a new enzyme, nucleoside oxidase, Agric. Biol. Chem. vol. 53, No. 6, pp. 1663–1669.*
Mudrakovskaya et al. RNA ligase of Bacteriophage T4. Bioorganicheskaya Kimiya, vol. 17, No. 6, pp. 819–822.*
Schmitz, C., et al., "Solid–phase enzymatic synthesis of oligonucleotides," Am. Chem. Soc., 1999, 1(11), 1729–1731.
Kikuchi, M. et al., "An effective family shuffling method using single–stranded DNA", Gene, 2000, 243, 133–137.
Vratskikh, LV. et al., "Solid–phase synthesis of oligoribonucleotides using T4 RNA ligase and T4 polynucleotide kinase", Biochimie, 1995, 77(4), 227–232.

(List continued on next page.)

Primary Examiner—Kenneth R. Horlick
Assistant Examiner—Teresa Strzelecka
(74) Attorney, Agent, or Firm—Woodcock Washburn LLP

(57) ABSTRACT

The present invention provides methods of preparing large polynucleotides of arbitrary sequence and in a manner that will readily lend itself to automation. The present invention provides methods of preparing a polynucleotide having at least 200 nucleotides in either a 5' to 3' or 3' to 5' direction by ligating a plurality of oligonucleotides, the assembly of which, represents the nucleotide sequence of the desired polynucleotide.

35 Claims, 2 Drawing Sheets

OTHER PUBLICATIONS

Nord, K. et al., "A combinatorial library of an alpha–helical bacterial receptor domain," *Protein Engineering*, 1995, 8(6), 601–608.

Rayner, S. et al., "MerMade: An oligodeoxyribonucleotide synthesizer for high throughput oligonucleotide production in dual 96–well plates," *PCR Methods and Applications*, Jul. 1998, 8(7), Cold Spring Harbor, NY, 741–747.

Chen, K., et al., "Tuning the activity of an enzyme for unusual environments: sequential random mutagenesis of subtilisin E for catalysis in dimethylformamide," *Proc. Natl. Acad. Sci. USA*, 1993, 90, 5618–5622.

Chen, K., et al., "Enzyme engineering for nonaqueous solvents: random mutagenesis to enhance activity of subtilisin E in polar organic media," *Biotechnology*, 1991, 9, 1073–1077.

Chu, B.C.F., et al., "Ligation of oligonucleotides to nucleic acids or proteins via disulfide bonds," *Nuc. Acids Res.*, 1988, 16(9), 3671–3691.

Delagrave, S., et al., "Recursive ensemble mutagenesis," *Protein Eng.*, 1993, 6, 327–331.

Harada, K., et al., "In vitro selectiion of optimal DNA substrates for T4 RNA ligase," *Proc. Natl. Acad. Sci., USA*, 1993, 90, 1576–1579.

Horn, T., et al., "A chemical 5'–phosphorylation of oligodeoxyribonucleotides that can be monitored by trityl cation release," *Tetra. Lett.*, 1986, 27, 4705–4708.

Isono, Y., et al., "Purification and reaction of a new enzyme, nucleoside oxidase," *Agric. Biol. Chem.*, 1989, 53, 1663–1669.

Joo, H., et al., "A high–throughput digital imaging screen for the discovery and directed evolution of oxygenases," *Chem. Biol.*, 1999, 6(10), 699–706.

Joo, H., et al., "Laboratory evolution of peroxide–mediated cytochrome P450 hydroxylation," *Nature*, 1999, 399, 670–673.

Leung, D. W., et al., "A method for random mutagenesis of a defined DNA segment using a modified polymerase chain reaction," *J. Methods in Cell and Molec. Biol.*, 1989, 1, 11–15.

Marrs, B., et al., "Novel approaches for discovering industrial enzymes," *Curr. Opin. Microbiol.*, 1999, 2, 241–245.

Miyazaki, K., et al., "Exploring nonnatural evolutionary pathways by saturation mutagenesis: rapid improvement of protein function," *J. Mol. Evol.*, 1999, 49, 716–720.

Mudrakovskaia, A.V., et al., "Solid–phase enzymatic synthesis of oligoribonucleotides," *Plenum Publ. Corp.*, 1992, translated from *Bioorganicheskaya Khimiya*, 17(6), 1991, 819–822; *Plenum Publishing Corp.*, 1992, 469–472.

Pantoliano, M..W., et al., "Large increases in general stability for subtilisin BPN' through incremental changes in the free energy of unfolding," *Biochemistry*, 1989, 28, 7205–7213.

Sambrook, et al. (eds.), *Molecular Cloning: A Laboratory Manual*, Cold Spring Harbor Laboratory Press, Cold Spring Harbor, NY, 1989.

Sambrook, et al., *Molecular Cloning a Laboratory Manual*, $2^{nd}$ Ed., cold Spring Harbor Press, 1989.

Tessier, D.C., et al., "Ligation of single–stranded oligodeoxyribonucleotides by T4 RNA ligase," *Analytical Bioc.*, 1986, 158, 171–178.

Uemura, A., et al., "Lipase–catalyzed regioselective acylation of sugar moieties of nucleosides," *Tetra. Letts.*, 1989, 30(29), 3817–3818.

Wong, C., et al., "Enzymes in organic synthesis: use of subtilisin and a highly stable mutant derived from multiple site–specific mutations," *J. Am. Chem. Soc.*, 1990, 112, 945–953.

You, L., et al., "Directed evolution of subtilisin E in *Bacillus subtilis* to enhance total activity in aqueous dimethylformamide," *Protein Eng.*, 1994, 9(1), 77–83.

Zhang, X., et al., "Single–stranded DNA ligation by T4 RNA ligase for PCR cloning of 5'–noncoding fragments and coding sequence of a specific gene," *Nuc. Acids Res.*, 1996, 24(5), 990–991.

Schmitz, C., et al., "Solid–phase enzymatic synthesis of oligonucleotides," *Am. Chem. Soc.*, 1999, 1(11), 1729–1731.

* cited by examiner

SOLID PHASE ENZYMATIC ASSEMBLY OF POLYNUCLEOTIDES

FIELD OF THE INVENTION

The present invention relates generally to processes for the synthesis of polynucleotides, such as DNA and fragments of DNA, RNA and fragments of RNA, plasmids, genes, and chemically and/or structurally modified polynucleotides.

BACKGROUND OF THE INVENTION

Living cells can be "reprogrammed," in vitro or in vivo, to produce useful amounts of desired proteins or other compounds by introducing the appropriate nucleic acids (DNA or RNA) into them; this concept is the keystone of modern biotechnology. The construction of recombinant DNA molecules necessary to achieve this "reprogramming" or to perform a varied and growing number of other functions is a frequent and necessary activity of molecular biology research and of biotechnological endeavors in industrial and academic settings. By improving the process by which DNA or RNA molecules of arbitrary sequence are made, a significant increase of productivity in biotechnology could be achieved, resulting in benefits in many fields including medical research, agriculture and the chemical industry. For example, numerous efforts to sequence the entire genomes of a variety of organisms (microbes, animals and plants) has generated many large databases of gene sequences. These genes can be made and studied experimentally through laborious and time-consuming techniques involving the isolation and subsequent manipulation (generally referred to as molecular cloning) of DNA from the organism in which the gene is found and/or expressed. Alternatively, inefficient DNA synthesis methods can be used, as described below.

The ability to synthesize large RNA or DNA molecules (e.g., entire genes) is of value to any endeavor that relies on recombinant DNA technology. As alluded to above, DNA molecules of arbitrary sequence can be synthesized in vitro. A solid phase method to synthesize oligonucleotides that is now widely used in commercial DNA synthesizers is reported in U.S. Pat. No. 4,458,066. Current DNA synthesizers, however, are limited to the production of relatively short single-stranded DNA oligonucleotide molecules of length typically less than 200 nucleotides (nt). In contrast, the average prokaryotic gene is 1000 basepairs (bp) in length, a eukaryotic cDNA is frequently longer than 2000 bp, and most plasmids are larger than 3000 bp. Although state-of-the-art oligonucleotide synthesizers relying on beta-cyanoethyl phosphoramidite chemistry (U.S. Pat. No. 5,935,527) can make and purify 48 oligonucleotides in less than 48 hours (25 nt/oligo×48 oligonucleotides=1200 nt, a typical bacterial gene), it is still very time consuming and labor-intensive to assemble these oligonucleotides together into a single gene.

Gene synthesis, a service frequently offered commercially by oligonucleotide manufacturers, is expensive (approximately $10 to $20/bp) and slow (frequently requiring several weeks) because current methods are labor-intensive. A method to make relatively large DNA molecules by mixing two long oligonucleotides (up to 400 nt) and amplifying the desired double-stranded DNA fragment from the mixture using the polymerase chain reaction (PCR) is reported in European Patent Application 90201671.6. This method becomes more complicated and requires extensive manipulations by a skilled technician when molecules larger than 400 bp must be synthesized. Similar statements can be made of the method of Khorana, *Science*, 1979, 203, 614–625.

A method to synthesize long nucleic acid molecules in which a ribo- or deoxyribo-oligonucleotide attached to a solid support is extended by the sequential addition of other "assembly" oligonucleotide is reported in U.S. Pat. No. 5,942,609. Of key importance to this process is the annealing of a partially complementary "bridging" oligonucleotide to the two oligonucleotides that will be covalently linked together by a ligase. Although this method will likely achieve its stated goal of synthesizing long polynucleotides, the need for the synthesis of a bridging oligonucleotide adds to the total number of oligonucleotides which must be synthesized and purified, with an attendant increase in costs and time of synthesis. In addition, the assembly of a complex mixture of oligonucleotides would greatly complicate this process because of the large number of different bridging oligonucleotides that would be needed to bring together the assembly oligonucleotides. Moreover, it would be advantageous to obviate the need for the annealing step required to productively bind the bridging oligonucleotide to its target assembly oligonucleotides. Such a step may introduce complications due to the need to avoid non-specific hybridization problems. Complications may include the need to carefully control hybridization temperatures over lengthy incubation periods as well as to carefully design each bridging oligonucleotides to bind specifically to the desired sequence.

International Publication WO83/02626 reports a method of assembling a polyribonucleotide using the enzyme T4 RNA ligase, including time-consuming purification steps, but does not include the use of solid phase methods which would facilitate automation and increase the reliability of the process. In contrast, Mudrakovskaia et al. (*Bioorg. Khim.*, 1991, 17, 819–822) report a "solid-phase enzymic synthesis of oligoribonucleotides" but do not disclose how the method could be used to couple more than a few nucleotides to a tethered oligonucleotide. Neither International Publication WO83/02626 nor Mudrakovskaia et al. disclose how their methods could be used to synthesize large (>200 nt) DNA or RNA molecules without requiring numerous and laborious purification steps.

Harada et al. (*Proc. Natl. Acad. Sci. USA*, 1993, 90, 1576–1579) reports in vitro selection techniques to characterize DNA sequences that are ligated efficiently by T4 RNA ligase. Tessier et al. (*Anal. Biochem.*, 1986, 158, 171–178) reports a set of reaction conditions for ligation of DNA fragments up to 40 bases in length. Zhang et al. (*Nuc. Acids Res.*, 1996, 24, 990–991) reports single-stranded DNA ligation by T4 RNA ligase for PCR cloning of 5' noncoding fragments and coding sequence of a particular gene.

A method of synthesizing large polynucleotides (such as RNA or DNA molecules longer than 200 bp) of arbitrary or predefined sequence and in a manner that will more readily lend itself to automation is desired. In addition, an improved version of the enzyme T4 RNA ligase that would increase the ability of this enzyme to catalyze the ligation of two oligonucleotides is also desired. Ideally, the improved enzyme would catalyze efficiently the ligation of oligonucleotides. Also, the ability of the enzyme to carry out these reactions at an elevated temperature or to use ddATP instead of ATP would be valuable properties in an improved ligase. By increasing the productivity of gene synthesis in laboratories, the present invention would improve scientists' ability to find, for example, enzymes capable of catalyzing reactions necessary to synthesize a new drug.

SUMMARY OF THE INVENTION

The present invention provides methods of preparing large polynucleotides (such as RNA or DNA molecules longer than 200 bp) of arbitrary sequence and in a manner that will more readily lend itself to automation than existing methods.

One aspect of the present invention is directed to methods of preparing a polynucleotide having at least 200 nucleotides and a predetermined nucleotide sequence comprising: providing a solid support, providing a plurality of oligonucleotides, wherein the combination of the nucleotide sequences of the oligonucleotides comprises the nucleotide sequence of the polynucleotide, contacting the solid support with the 3' terminus of a first oligonucleotide from the plurality of oligonucleotides to form a tethered oligonucleotide, ligating the 3' terminus of another oligonucleotide from the plurality of oligonucleotides to the 5' terminus of the tethered oligonucleotide, and repeating the ligation with other oligonucleotides until the polynucleotide is prepared.

Another aspect of the present invention is directed to methods of preparing a polynucleotide having at least 200 nucleotides and a predetermined nucleotide sequence comprising: providing a solid support, providing a plurality of oligonucleotides, wherein the combination of the nucleotide sequences of the oligonucleotides comprises the nucleotide sequence of the polynucleotide, contacting the solid support with the 5' terminus of a first oligonucleotide from the plurality of oligonucleotides to form a tethered oligonucleotide, ligating the 5' terminus of another oligonucleotide from the plurality of oligonucleotides to the 3' terminus of the tethered oligonucleotide, and repeating the ligation with other oligonucleotides until the polynucleotide is prepared.

DESCRIPTION OF PREFERRED EMBODIMENTS OF THE INVENTION

Figure 1:
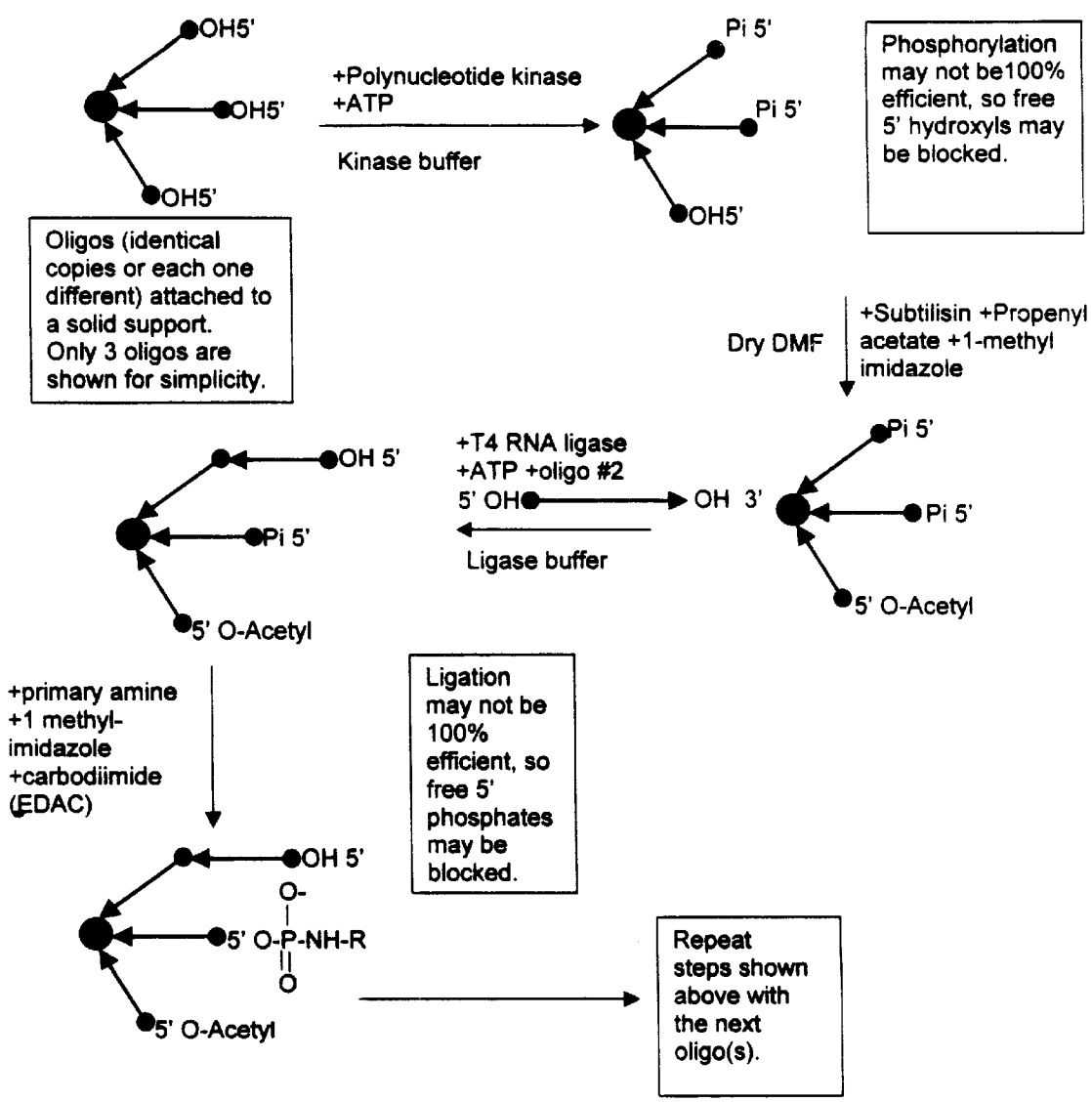
FIG. 1 shows a representative scheme for preparing a polynucleotide in the 3' to 5' direction.

The present invention provides, inter alia, methods of preparing large polynucleotides (such as RNA or DNA molecules longer than 200 bp) of arbitrary or predefined sequence. This process consists of the sequential assembly of oligonucleotides into a large polynucleotide through the use of enzymes (or other catalysts), uncatalyzed chemical reactions, and solid phase synthesis methods.

As used herein, the term "about" means ±5% of the value it modifies.

As used herein, the term "polynucleotide" means a polymer of nucleotides including ribonucleotides and deoxyribonucleotides, and modifications thereof, and combinations thereof. Preferred nucleotides include, but are not limited to, adenine, guanine, cytosine, thymine, and uracil. Modified nucleotides include, but are not limited to, 4-acetylcytidine, 5-(carboxyhydroxylmethyl)uridine, 2O-methylcytidine, 5-carboxymethylaminomethyl-2-thiouridine, 5-carboxymethylamino-methyluridine, dihydrouridine, 2-O-methylpseudouridine, 2-O-methylguanosine, inosine, N6-isopentyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, 5-methoxyuridine, 5-methoxycarbonylmethyl-2-thiouridine, 5-methoxycarbonylmethyluridine, 2-methylthio-N6-isopentenyladenosine, uridine-5-oxyacetic acid-methylester, uridine-5-oxyacetic acid, wybutoxosine, wybutosine, pseudouridine, queuosine, 2-thiocytidine, 5-methyl-2-thiouridine, 2-thiouridine, 4-thiouridine, 5-methyluridine, 2-O-methyl-5-methyluridine, 2-O-methyluridine, and the like. The polynucleotides of the invention can also comprise both ribonucleotides and deoxyribonucleotides in the same polynucleotide (e.g. a chimera).

As used herein, the term "oligonucleotide" means a polymer of nucleotides including ribonucleotides and deoxyribonucleotides, and modifications thereof, and combinations thereof, as described above. The polynucleotides of the invention comprise a plurality of oligonucleotides.

As used herein, the phrase "tethered oligonucleotide" means an oligonucleotide that is attached to a solid support or an oligonucleotide attached to a compound that is soluble under certain conditions (facultative solid). An example of such a compound is a plasmid (or any other large DNA molecule) that is soluble in water or buffer but insoluble in a cold (<4° C.) solution of 0.3 M sodium acetate and ~70% ethanol.

As used herein, the term "viroid" means a viral polynucleotide.

The present invention is directed to methods of preparing a polynucleotide having at least 200 nucleotides and having a predetermined nucleotide sequence. Preferably, the polynucleotide comprises at least 200 nucleotides. More preferably, the polynucleotide comprises between about 400 nucleotides and about 100,000 nucleotides, more preferably between about 750 nucleotides and about 50,000 nucleotides, and even more preferably between about 1000 nucleotides and 10,000 nucleotides. The polypeptide can be RNA, DNA, or a combination thereof. The polynucleotide is preferably a gene, a portion of a gene, or a plasmid, cosmid, viral genome, bacterial genome, mammalian genome, origins of replication, and the like.

A polynucleotide having a predetermined nucleotide sequence comprising N nucleotides, whose synthesis is desired, is dissected into a plurality of contiguous oligonucleotide fragments of at least two nucleotides and at most N-2 nucleotides. The length of the oligonucleotides can vary as desired, but can be between about 10 nucleotides and about 150 nucleotides, more preferably between about 15 nucleotides and 100 nucleotides, and more preferably between about 25 nucleotides and 75 nucleotides. A convenient oligonucleotide length, for example, may be 100 nucleotides, such that, for example, a 2000 bp polynucleotide will be synthesized by the assembly of 20 contiguous oligonucleotides. Although it is convenient to dissect a polynucleotide into oligonucleotide fragments of equal size, this is not necessary. Each of the oligonucleotides can be prepared using commercially available methods using conventional technology such as, for example, nucleic acid synthesizers. Although purification of the synthesized oligonucleotides may not be necessary, such a step will generally increase the yield of the desired polynucleotide final product. Oligonucleotide suppliers can perform synthesis and purification at reasonable rates.

The set of contiguous oligonucleotide fragments derived from the dissected polynucleotide having nucleotide sequences which, when assembled in order, correspond to the entire nucleotide sequence of the polynucleotide make up the "plurality of oligonucleotides." Preferably, the oligonucleotides within the plurality of oligonucleotides are in solution. It is the combination, or assembly, of the nucleotide sequences of each of the oligonucleotide fragments that comprises the entire nucleotide sequence of the polynucleotide desired to be prepared. In addition, if a degenerate set of polynucleotides encoding a particular protein is desired to be prepared, a set of degenerate oligonucleotides can be prepared accordingly. Thus, for example, a set of 3'-most oligonucleotides can be prepared where, for example, the third position within a codon varies. Such a set can be prepared for each oligonucleotide within the polynucleotide such that all possible combinations of degenerate polynucleotides are produced.

In some embodiments of the invention, the 5' terminus of one or more of the oligonucleotides within the plurality of oligonucleotides is phosphorylated during or after the synthesis of the oligonucleotide. Thus, one or more of the oligonucleotides within the plurality of oligonucleotides can be phosphorylated prior to contacting the oligonucleotide with the solid support. Phosphorylation can be achieved by methods known to those skilled in the art including, but not limited to, using a phosphoramidite or kinase.

The oligonucleotides can be immobilized on a solid support through any number of well known covalent linkages or non-covalent interactions. A preferred solid support is selected from the group consisting of, but not limited to, agarose, polyacrylamide, magnetic beads, polystyrene, polyacrylate, controlled-pore glass, hydroxyethylmethacrylate, polyamide, polyethylene, polyethyleneoxy, polyethyleneoxy/polystyrene copolymer, and the like. Additional examples of solid support and methods of immobilizing oligonucleotides thereto are described in, for example, U.S. Pat. No. 5,942,609, which is incorporated herein by reference in its entirety.

In one embodiment of the invention, preparation of the polynucleotide can be achieved in the 3' to 5' direction. The solid support is contacted with the 3' terminus of a first oligonucleotide from the plurality of oligonucleotides to form a tethered oligonucleotide. The first oligonucleotide is, thus, the 3' most oligonucleotide fragment of the polynucleotide. The first oligonucleotide is attached to the solid support such that its 5'-OH or 5' phosphate functional group is available to react further in the process. This linkage to a solid support can be achieved in a number of different ways as described in, for example, U.S. Pat. No. 5,942,609. As described above, the 5' terminus of this oligonucleotide can be phosphorylated prior to contacting the oligonucleotide with the solid phase. Alternately, the 5' terminus of the oligonucleotide can be phosphorylated after contacting the oligonucleotide with the solid phase. In this manner, it is the 5' terminus of the tethered oligonucleotide that is phosphorylated. Such phosphorylation can be carried out, for example, with a phosphoramidite (Horn et al., Tetrahedron Lett., 1986, 27, 4705–4708, which is incorporated herein by reference in its entirety) or through the use of enzymes such as, but not limited to, polynucleotide kinases which require ATP and various salts.

Phosphorylation of the 5' termini of oligonucleotides may not always be 100% efficient. Whether phosphorylated oligonucleotides are immobilized to the solid support or whether unphosphorylated oligonucleotides are immobilized to the solid support and subsequently phosphorylated, some of the tethered oligonucleotides may not comprise a phosphorylated 5' terminus. Thus, contaminating oligonucleotide assembly products may be produced. In order to minimize the contamination, an optional step in the process can be performed in which the 5' termini are chemically modified in such a way as to prevent their reaction in further steps of the polynucleotide assembly process. Thus, in some embodiments of the invention, prior to ligation of the tethered oligonucleotide to another oligonucleotide within the plurality of oligonucleotides, the tethered oligonucleotide having an unphosphorylated 5' terminus can be capped. Such an optional capping step has no impact on a tethered oligonucleotide which has a phosphorylated 5' terminus. The 5'—OH can be prevented from undergoing inappropriate phosphorylation by a variety of means. Such means include, but are not limited to, use of enzymes which oxidize 5' hydroxyls (e.g., nucleoside oxidase, E.C.1.1.3.28; Isono et al., Agric. Biol. Chem., 1989, 53, 1663–1669, which is incorporated herein by reference in its entirety). Alternately, capping can be carried out with an enzyme that acylates the 5'—OH terminus of the unphosphorylated tethered oligonucleotide. A preferred enzyme is, but is not limited to, a lipase (Uemura et al., Tetrahedron Lett., 1989, 30, 3817–3818, which is incorporated herein by reference in its entirety) or subtilisin (Wong et al., J. Am. Chem. Soc., 1990, 112, 945–953, which is incorporated herein by reference in its entirety), or the like. In addition, particular chemicals known to those skilled in the art can also achieve the desired modification. The capping step may not be necessary to produce useful amounts of the desired full-length polynucleotide.

Once the tethered oligonucleotide is formed, the 3' terminus of another oligonucleotide within the plurality of oligonucleotides, the penultimate 3' oligonucleotide fragment within the polynucleotide, is ligated to the phosphorylated 5' terminus of the tethered oligonucleotide. Ligation can be carried out by co-incubating a ligase, the tethered oligonucleotide, and another oligonucleotide to be ligated to the tethered oligonucleotide. ATP as well as other buffer components are also added (Tessier et al., Anal. Biochem., 1986, 158, 171–178, which is incorporated herein by reference in its entirety; and International Publication WO83/02626, which is incorporated herein by reference in its entirety), as is usually necessary for ligases. The ligation can be carried out with any ligase known to those skilled in the art. Preferably, the ligase is, but is not limited to, an RNA ligase or a ribozyme. More preferably, the RNA ligase is T4 RNA ligase or modified T4 RNA ligase. T4 RNA ligase has been shown to catalyze the ligation of oligonucleotides (Tessier et al., supra, and Shizuya, supra), however, other catalysts can be used. For example, genetically modified versions of T4 RNA ligase with enhanced catalytic activity can be engineered using, for example, methods of directed evolution. The process of directed evolution or in vitro evolution (ive) has been described in detail (Joo et al., Chem. Biol., 1999, 6, 699–706; Joo et al., Nature, 1999, 399, 670–673; Miyazaki et al., J. Mol. Evol., 1999, 49, 716–720; Chen et al., Proc. Natl. Acad. Sci. USA, 1993, 90, 5618–5622; Chen et al., Biotechnology, 1991, 9, 1073–1077; You et al., Protein Eng., 1996, 9, 77–83; each of which is incorporated herein by reference in its entirety). In general, the method involves the steps of 1) creating a population of mutant genes; 2) screening this population for individual genes which have a desired property such as coding for an enzyme with improved activity; 3) introducing mutations in the improved gene to create a new population of mutants, and 4) repeating steps 2 and 3 until a desired improvement is achieved. Many methods to introduce mutations exist and are described in the literature (Leung et al.,

*Technique*, 1989, 1, 11–15; Delagrave et al., *Protein Eng.*, 1993, 6, 327–331; each of which is incorporated herein by reference in its entirety). Similarly, there are many ways to screen mutants for a desired property (Joo et al., *Chem. Biol.*, 1999, 6, 699–706; Joo et al., *Nature*, 1999, 399, 670–673; Miyazaki et al., *J. Mol. Evol.*, 1999, 49, 716–720; Chen et al., *Proc. Natl. Acad. Sci. USA*, 1993, 90, 5618–5622; Chen et al., *Biotechnology*, 1991, 9, 1073–1077; You et al., *Protein Eng.*, 1996, 9, 77–83; Marrs et al., *Curr. Opin. Microbiol.*, 1999, 2, 241–245; and U.S. Pat. No. 5,914,245). Improvements in the properties of enzymes (e.g., half-life in organic solvents) achieved using the methods described in the references listed above are frequently one order of magnitude (ten-fold) or greater. Alternatively, ribozymes may be used to ligate oligonucleotides efficiently. Modification of T4 RNA ligase is described below in Example 5. In some embodiments of the invention, the 5' terminus of another oligonucleotide within the plurality of oligonucleotides (e.g., the penultimate 3' oligonucleotide fragment) is phosphorylated prior to ligation to the tethered oligonucleotide. In other embodiments of the invention, the 5' terminus of another oligonucleotide of the plurality of oligonucleotides (e.g., the penultimate 3' oligonucleotide fragment) is not phosphorylated prior to ligation with the tethered oligonucleotide.

Ligation reactions may not be 100% efficient. As a result, contaminating oligonucleotide assembly products missing one or more oligonucleotides can be produced. To void excessive accumulation of such assembly products, another optional step can be performed in which the 5' phosphate groups of unligated polynucleotides attached to the solid support are chemically modified in such a way as to prevent their reaction in further steps of the polynucleotide assembly process. The 5' phosphate can be prevented from undergoing further ligation reactions by a variety of means. In some embodiments of the invention, after ligation of the phosphorylated tethered oligonucleotide to another oligonucleotide within the plurality of oligonucleotides, the phosphorylated 5' terminus of any unligated tethered oligonucleotide can be capped. Capping can be carried out by, but not limited to, forming a phosphamide or reaction with a blocking oligonucleotide or the like. Preferably, the blocking oligonucleotide is, but is not limited to, a 5'deoxyoligonucleotide or an oligonucleotide comprising a 5' fluorescent label or other similar blocking agent. Such fluorescent labels are well known to those skilled in the art. A preferred method to block unligated polynucleotides is to form a phosphamide (Chu et al., *Nuc. Acids Res.*, 1988, 16, 3671–3691, which is incorporated herein by reference in its entirety). This is achieved by mixing a solution containing a primary amine, a carbodiimide and, for example, 1-methyl-imidazole with the oligonucleotides attached to the solid support. This capping step may not be necessary to produce useful amounts of the desired full-length polynucleotide. In this manner, those tethered oligonucleotides which failed to undergo a successful ligation with another oligonucleotide within the plurality of oligonucleotides will have a 5' capped terminus that is incapable of allowing the 5' tethered oligonucleotide to be successfully ligated to any other oligonucleotide within the plurality of oligonucleotides.

The ligation steps are repeated with successive contiguous oligonucleotides within the plurality of oligonucleotides until the polynucleotide is prepared. The steps of phosphorylation, capping of unphosphorylated tethered oligonucleotide, and capping of unligated tethered oligonucleotide outlined above can also be repeated, if necessary, to assemble the tethered polynucleotide of the desired length and sequence. Thus, the 5'-most oligonucleotide will be the last oligonucleotide within the plurality of oligonucleotides to be ligated to the ever-elongating tethered oligonucleotide. In some embodiments of the invention, a plurality of different oligonucleotides are contacted with the solid phase simultaneously in order to prepare a plurality of polynucleotides. Between each of the above steps, washes may be necessary to eliminate unreacted compounds and other non-covalently bound contaminants. Also, denaturation steps (e.g., using heat or chemicals such as sodium hydroxide, urea, formamide, etc.) can be added to eliminate oligonucleotides bound non-specifically to the growing polynucleotide chain. Preparation of polynucleotides of the invention in a 3' to 5' direction is summarized in FIG. 1.

In another embodiment of the invention, preparation of the polynucleotide can be achieved in the 5' to 3' direction. The solid support is contacted with the 5' terminus of a first oligonucleotide from the plurality of oligonucleotides to form a tethered oligonucleotide. The first oligonucleotide is, thus, the 5' most oligonucleotide fragment of the polynucleotide. The first oligonucleotide is attached to the solid support such that its 3'—OH group is available to react further in the process with the 5' phosphate group of another oligonucleotide. This linkage to a solid support can be achieved in a number of different ways as described in, for example, U.S. Pat. No. 5,942,609.

The 5' terminus of the remaining oligonucleotides within the plurality of oligonucleotides is phosphorylated prior to contacting the oligonucleotide with the tethered oligonucleotide. Such phosphorylation can be carried out, for example, with a phosphoramidite or kinases as described above. In some embodiments of the invention, the 3' terminus of the oligonucleotide within the plurality of oligonucleotides is blocked in order to avoid self-ligation. Such blocking is carried out by, but not limited to, phosphorylation or using enzymes such as, for example, subtilisin or lipases, which acylate the 3'OH terminus of the oligonucleotide, as described above for 3' to 5' synthesis. This 3' phosphorylation can conveniently be performed by phosphoramidite chemistry as part of the synthesis of the oligonucleotide. Use of these enzymes, however, would preclude the use of acylation as a means of capping unligated oligonucleotides described below. 3' acylation can be performed during the synthesis of the oligonucleotide.

Once the tethered oligonucleotide is formed, the 5' terminus of another oligonucleotide within the plurality of oligonucleotides, the second 5' oligonucleotide fragment within the polynucleotide, is ligated to the 3' terminus of the tethered oligonucleotide. Ligation of the 5' terminus of an oligonucleotide from within the plurality of oligonucleotides to the 3' terminus of the tethered oligonucleotide can be carried out using ligases or ribozymes, as described above. For example, ligation can be achieved by co-incubating a ligase, the tethered oligonucleotide, and the oligonucleotide to be ligated to it. ATP as well as other buffer components are also added, as is usually necessary for ligases. Any of the ligases described above can be used.

As described above for the 3' to 5' synthesis, this ligation reaction may not be 100% efficient. As a result, contaminating oligonucleotide assembly products missing one or more oligonucleotides can be produced. To avoid excessive accumulation of failed sequences, a capping step can be performed wherein the 3'—OH groups of unligated polynucleotides attached to the solid support are chemically modified in such a way as to prevent their reaction in further steps of the polynucleotide assembly process. In some embodiments of the invention, after ligation of another oligonucleotide within the plurality of oligonucleotides, wherein the oligonucleotide comprises a blocked 3' terminus, as described above, to the tethered oligonucleotide, the 3' terminus of any unligated tethered oligonucleotide is capped. In this manner, only unligated tethered oligonucleotides will be capped; ligated tethered oligonucleotides will have a 3' blocking group which is unable to be capped. Capping can be carried out with, for example, an enzyme that acylates the 3'—OH terminus of the unligated tethered oligonucleotide including, but not limited to, a lipase or subtilisin. Alternately, capping can be carried out with an enzyme that adds at least one dideoxy nucleotide to the 3' terminus of the unligated tethered oligonucleotide including, but not limited to, terminal transferase (or any other enzyme with a similar activity). The capping step may not be necessary to produce useful amounts of the desired full-length polynucleotide.

In order for the tethered oligonucleotide to undergo a second ligation to another oligonucleotide within the plurality of oligonucleotides, the 3' blocking moiety must be removed. Thus, in some embodiments of the invention, after ligation of the tethered oligonucleotide to another oligonucleotide having a blocked 3' terminus, the blocked 3' terminus is deblocked. Deblocking can be carried out, for example, by using any adequate phosphatase such as alkaline phosphatase, in the case of a phosphate group, or an enzyme such as, but not limited to, phosphatase, subtilisin, lipase, or the like, in aqueous solvent in the case where the oligonucleotide is blocked by 3' acylation.

Figure 2:
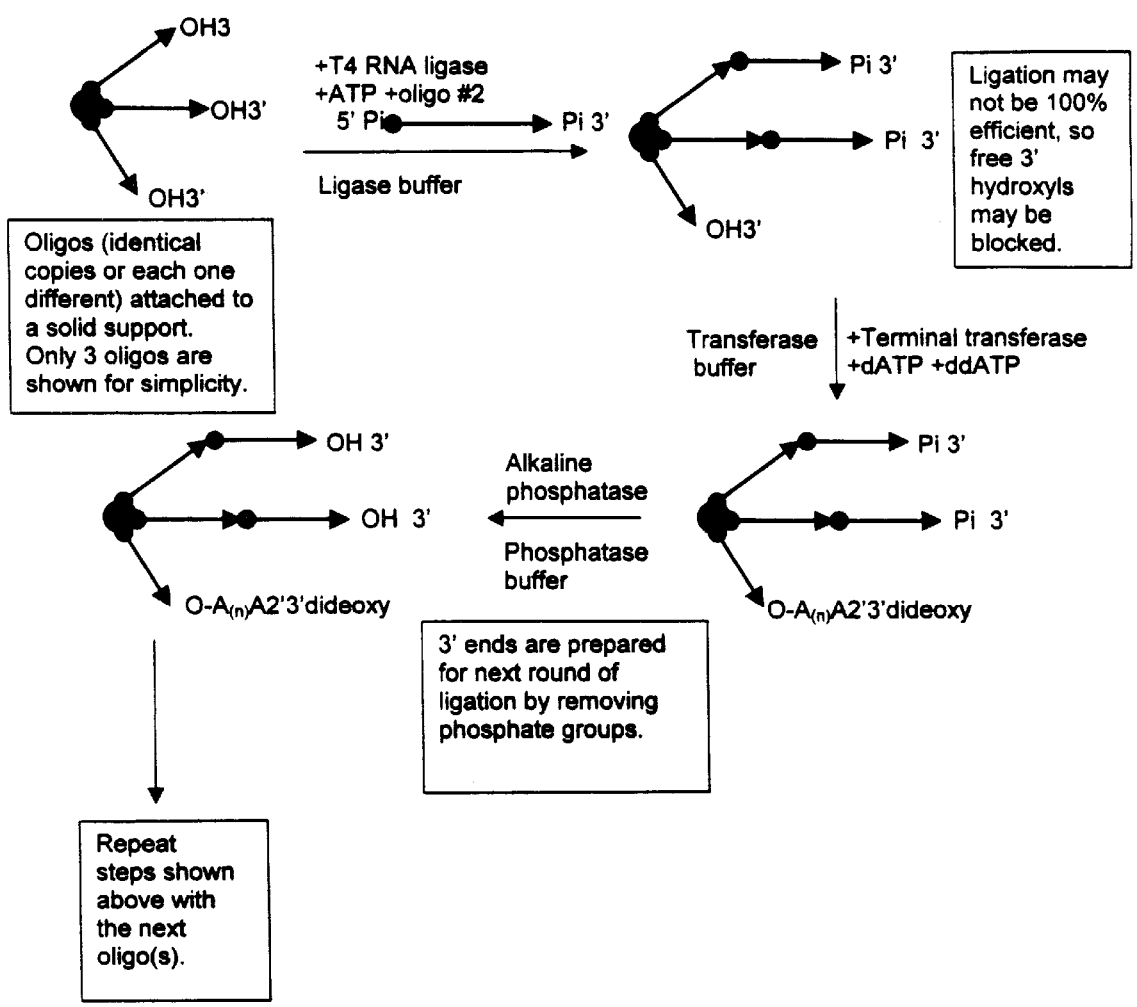
FIG. 2 shows a representative scheme for preparing a polynucleotide in the 5' to 3' direction.

The ligation steps are repeated with successive contiguous oligonucleotides within the plurality of oligonucleotides until the polynucleotide is prepared. The steps of ligation, capping of unligated tethered oligonucleotide, and deblocking outlined above can also be repeated, if necessary, to assemble the tethered polynucleotide of the desired length and sequence. Thus, the 3'-most oligonucleotide will be the last oligonucleotide within the plurality of oligonucleotides to be ligated to the ever-elongating tethered oligonucleotide. In some embodiments of the invention, a plurality of different oligonucleotides are contacted with the solid phase simultaneously in order to prepare a plurality of polynucleotides. Between each of the above steps, washes may be necessary to eliminate unreacted compounds and other non-covalently bound contaminants. Also, denaturation steps (e.g., using heat or chemicals such as sodium hydroxide, urea, formamide, etc.) can be added to eliminate oligonucleotides bound non-specifically to the growing polynucleotide chain. Between each of the above steps, washes may be necessary to eliminate unreacted compounds and other non-covalently bound contaminants. Also, denaturation steps (e.g., using heat or chemicals such as sodium hydroxide, urea, formamide, etc.) can be added to eliminate oligonucleotides bound non-specifically to the growing polynucleotide chain. Preparation of polynucleotides of the invention in a 5' to 3' direction is summarized in FIG. 2.

Following completion of the synthesis of the polynucleotide, depending on the particular solid support and linker, the polynucleotide can be cleaved from its solid support for processing following synthesis. Cleavage may not be necessary, depending on the solid support and linker, for PCR or RT-PCR to be carried out on the tethered polynucleotide. A polynucleotide encoding all genetic elements necessary for it to be inherited in a stable fashion upon division of its host cell can simply be cleaved from its solid support, circularized by ligation if necessary, and transformed into such a host without any need for amplification or purification. For example, a polynucleotide corresponding to the sequence of LITMUS28 (2,823 bp; New England Biolabs, Beverly, Mass.) can be synthesized, circularized by ligation and transformed into the appropriate strain of *E. coli*. The presence of the M13 origin of replication on this phagemid will allow its single-stranded circular form to replicate in its host, and the ampicillin resistance marker will allow for a selection to isolate only those cells which were transformed by a viable copy of the phagemid. All necessary methods to perform these manipulations can be found in Sambrook, et al., (Eds.), *Molecular Cloning: A Laboratory Manual*, Cold Spring Harbor Laboratory Press: Cold Spring Harbor, N.Y. (1989). The desired polynucleotide can be amplified using the polymerase chain reaction (PCR). If the polynucleotide is an RNA molecule, reverse-transcription-PCR (RT-PCR) can be used to amplify the desired product. PCR or RT-PCR products of the expected molecular weight can be purified by gel electrophoresis. The resulting double-stranded DNA can be used in a variety of experiments, but can also be transformed into a eukaryotic or prokaryotic host such as *E. coli* after adequate preparation as would be obvious to anyone skilled in the art.

Some of the preferred embodiments of the invention described above are outlined below and include, but are not limited to, the following embodiments. As those skilled in the art will appreciate, numerous changes and modifications may be made to the preferred embodiments of the invention without departing from the spirit of the invention. It is intended that all such variations fall within the scope of the invention.

EXAMPLES

Example 1

3' to 5' Assembly of a 1000 bp Polynucleotide With No Capping

During the incubations described below, the reaction vessel is tumbled end-over-end to keep the beads in suspension.

Step 1. Synthesis. Twenty oligonucleotides, each 50 nucleotides in length are synthesized, deprotected and purified by HPLC according to standard methods. Each oligonucleotide is numbered according to its position in the sequence of the polynucleotide to be synthesized, with the 3'-most oligonucleotide being number 1 and the 5'-most being number 20. Using standard phosphoramidite chemistry, a linker containing a primary amine is attached to the 3'—OH of Oligo #1. The linker is attached such that its amine functional group is free to react with the solid support functional groups during the immobilization step (see below). The linker could be cystamine or an analogous compound with a primary amine at each end of an alkyl chain that contains a disulfide, but reducing agents should then be avoided in subsequent steps of this protocol. The necessary oligonucleotides can be purchased from a commercial supplier such as Operon Inc., or Sigma Inc. All oligonucleotide should have free 5'—OH groups.

Step 2. Immobilization. This step is performed essentially according to the manufacturer's instructions (Pierce Chemical co., Rockford Ill.). For example: In a 1.5 ml microcentrifuge tube, 0.1 μmol of Oligo #1, dissolved in 500 μl conjugation buffer containing 0.1 M MES (N-morpholinoethane sulfonic acid) pH 4.7, 0.9% NaCl, is added to 10 mg of Magnabind carboxyl-derivatized magnetic beads prewashed with 1×PBS containing 100 mM phosphate (pH 7.2) and 150 mM NaCl. Fifty μl of 10 mg/ml EDC (1-ethyl-3-(3-dimethylaminopropyl)carbodiimide) is added to the mixture and incubated for 30 minutes at room temperature (20–25° C). Unreacted COOH groups on the beads can be quenched with a primary amine such as ethylamine or ethanolamine. The amount of Oligo #1 added to the beads can be varied in order to achieve the coupling of ~0.1 μmol of Oligo #1 to the 10 mg of beads.

Step 3. Wash. Unbound oligonucleotides are washed away by removing the solution present in the tube, adding 1 ml of wash buffer W1 containing 25 mM Tris-HCl, pH 7.5, 125 mM NaCl and 1 g/L Tween-20® (polyoxyethylenesorbitan monolaurate), and removing the wash buffer. This wash is performed twice. A final wash using 1 ml of buffer W2 containing 50 mM Tris-Cl pH 8.2, 10 mM $MgCl_2$, 0.1 mM EDTA, 5 mM dithiothreitol, 0.1 mM spermidine is performed. The Magnabeads are conveniently precipitated to the bottom of the microcentrifuge tube by using a magnetic field according to the manufacturer's instructions.

Step 4. Phosphorylation. Oligo #1 (now attached to the solid support) is phosphorylated at its 5'—OH group by adding to the tube 500 μl of buffer P (containing: 50 mM Tris-Cl pH 8.2, 10 mM $MgCl_2$, 0.1 mM EDTA, 5 mM dithiothreitol, 0.1 mM spermidine, 0.4 mM ATP and 200 units of polynucleotide kinase from Roche Molecular Biochemicals) and incubating for 30 minutes at 37° C. (If Oligo #1 was already phosphorylated, this step is not necessary.)

Step 5. Wash. Reagents from the previous step are removed (e.g., by aspiration) and the beads are washed three times with ligation buffer L (minus the ATP and ligase). Finally, the beads are resuspended in 500 μl of buffer L (composition described in step 6) and transferred to a 10 ml conical tube.

Step 6. Ligation. 0.5 μmol of Oligo #2, dissolved in 4.5 ml of buffer L (containing: 50 mM Tris-HCl, pH 8.0, 10 mM $MgCl_2$, 10 μM BSA, 25% polyethylene glycol (PEG 8000), 1 mM hexamine cobalt chloride (HCC), 20 μM ATP and 2000 units of T4 RNA ligase (Roche)) is added to the tube containing the beads and incubated for 4 hours at 25° C.

Alternatively, the beads can be resuspended in 1 ml of buffer L containing 0.5 μmol of Oligo #2 and only 400 units of T4 RNA ligase, incubated for 1 hour at 25° C., precipitated to the bottom of the tube and resuspended in a fresh 1 ml aliquot of buffer L containing 0.5 μmol of Oligo #2 and 400 units of T4 RNA ligase. This procedure is performed a total of 5 times.

Another possibility is to resuspend the beads in 1 ml of buffer L containing 2000 units of T4 RNA ligase and 1 mM ddATP, instead of ATP, and performing a single 4 hour-long incubation at 25° C.

Step 7. Denaturation and wash. The beads are pelleted, and the contents of the tube are removed and 500 μl of wash buffer W1 is added. Without removing wash buffer W1, 500 μl of denaturation buffer containing 0.1 M NaOH and 300 mM NaCl is added into the tube for 1–2 minutes to denature the nascent polynucleotides and fortuitously hybridized oligonucleotides. The beads are then washed twice with 1 ml of wash buffer X containing 0.25 M Tris-HCl, pH 7.5, 0.125 M NaCl, 2 mM $MgCl_2$ and 3 g/l Tween-20®, and once with 1 ml of buffer W2.

Step 8. The nascent polynucleotide is phosphorylated and washed as in steps 4 and 5.

Step 9. The next oligonucleotide (Oligo #n) to be ligated to the nascent polynucleotide is added and incubated as in step 6.

Step 10. Denaturation and wash are performed as in step 7. Steps 8 through 10 are repeated as many times as is necessary to assemble the entire polynucleotide. A total of 19 ligation steps are performed to assemble 20 oligonucleotides.

Step 11. Elution. If the linker used in step 1 was cystamine, 2-mercaptoethanol can be used to elute the polynucleotides from the solid support. A 500 μl volume of solution containing 2-mercaptoethanol 0.1 M, dissolved in buffer W1 is added to the beads and incubated for 30 minutes at room temperature. The resulting solution is removed from the beads and transferred to a tube. Ethanol precipitation can be used to partially purify the polynucleotide, and the sample can be stored at –20° C. until needed. Alternatively, a nucleic acid purification kit (Qiaquick purification kit from Qiagen Inc.) can be used to purify and concentrate the polynucleotide.

Step 12. Amplification. An aliquot representing 10 to 50% of the partially purified eluate from step 11 is used as the template of a polymerase chain reaction (PCR). High-fidelity polymerases such as Pfu (Stratagene), Vent (New England Biolabs, Beverly Mass.) or Pwo (http://www.genaxis.com/) can be used in the PCR according to the manufacturers' recommendations. The resulting PCR product is electrophoresed on an agarose gel to allow the isolation of a useful quantity (>10 ng) of a 1 kb double-stranded DNA molecule. This DNA is cloned using methods known to those skilled in the art by using routine methods described in, for example, Sambrook et al. *Molecular Cloning a Laboratory Manual*, Second Ed. Cold Spring Harbor Press (1989) which is incorporated herein by reference in its entirety.) Alternative uses such as in vitro transcription and translation are possible.

Example 2

3' to 5' Assembly of a 1000 bp Polynucleotide With Capping

During the incubations described below, the reaction vessel is tumbled end-over-end to keep the beads in suspension.

Step 1. Synthesis. Twenty oligonucleotides, each 50 nucleotides in length are synthesized, deprotected and purified by HPLC according to standard methods. Each oligonucleotide is numbered according to its position in the sequence of the polynucleotide to be synthesized, with the 3'-most oligonucleotide being number 1 and the 5'-most being number 20. Using standard phosphoramidite chemistry, a linker containing a primary amine is attached to the 3'—OH of Oligo #1. The linker is attached such that its amine functional group is free to react with the solid support functional groups during the immobilization step (see below). The linker could be cystamine or an analogous compound with a primary amine at each end of an alkyl chain that contains a disulfide, but reducing agents should then be avoided in subsequent steps of this protocol. The necessary oligonucleotides can be purchased from a commercial supplier such as Operon Inc., or Sigma Inc. All oligonucleotides should have free 5' OH groups.

Step 2. Immobilization. This step is performed essentially according to the manufacturer's instructions (Pierce Chemical co., Rockford Ill.). For example: In a 1.5 ml microcentrifuge tube, 0.1 μmol of Oligo #1, dissolved in 500 μl conjugation buffer containing 0.1 M MES (N-morpholinoethane sulfonic acid) pH 4.7, 0.9% NaCl, is added to 10 mg of Magnabind carboxyl-derivatized magnetic beads prewashed with 1×PBS containing 100 mM phosphate (pH 7.2) and 150 mM NaCl. Fifty μl of 10 mg/ml EDC (1-ethyl-3-(3-dimethylaminopropyl)carbodiimide) is added to the mixture and incubated for 30 minutes at room temperature (20–25° C.). Unreacted COOH groups on the beads can be quenched with a primary amine such as ethylamine or ethanolamine. The amount of Oligo #1 added to the beads can be varied in order to achieve the coupling of ~0.1 µmol of Oligo #1 to the 10 mg of beads.

Step 3. Wash. Unbound oligonucleotides are washed away by removing the solution present in the tube, adding 1 ml of wash buffer W1 containing 25 mM Tris-HCl, pH 7.5, 125 mM NaCl and 1 g/L Tween-20®, and removing the wash buffer. This wash is performed twice. A final wash using 1 ml of buffer W2 containing 50 mM Tris-Cl pH 8.2, 10 mM $MgCl_2$, 0.1 mM EDTA, 5 mM dithiothreitol, 0.1 mM spermidine is performed. The Magnabeads are conveniently precipitated to the bottom of the microcentrifuge tube by using a magnetic field according to the manufacturer's instructions.

Step 4. Phosphorylation. Oligo #1 (now attached to the solid support) is phosphorylated at its 5'—OH group by adding to the tube 500 µl of buffer P (containing: 50 mM Tris-Cl pH 8.2, 10 mM $MgCl_2$, 0.1 mM EDTA, 5 mM dithiothreitol, 0.1 mM spermidine, 0.4 mM ATP and 200 units of polynucleotide kinase from Roche Molecular Biochemicals USA) and incubating for 30 minutes at 37° C. (If Oligo #1 was already phosphorylated, this step is not necessary.)

Step 5. Wash. Reagents from the previous step are removed (e.g., by aspiration) and the beads are washed twice with buffer W1 and twice with dry DMF (dimethyl formamide).

Step 6. Capping of non-phosphorylated 5'—OH. The beads are resuspended in 1 ml of DMF containing 100 µmol (11 µl) of isopropenyl acetate and 1 mg of subtilisin 8350 and incubated up to 24 hours at 45° C. Subtilisin is a thermostable enzyme described by Pantoliano et al. (*Biochemistry*, 1989, 28, 7205–13, which is incorporated herein by reference in its entirety) that can be constructed as described and prepared according to Wong et al. (*J. Am. Chem. Soc.*, 1990, 112, 945–953) and references listed therein. Thermostable subtilisins (e.g., Esperase) can also be purchased from Novo Nordisk (Denmark).

Step 7. Wash. Reagents from the previous step are removed (e.g., by aspiration) and the beads are washed once with 1 ml of DMF and three times with ligation buffer L (without the ATP and ligase). Finally, the beads are resuspended in 500 µl of buffer L (composition described in step 6) and transferred to a 10 ml conical tube.

Step 8. Ligation. 0.5 µmol of Oligo #2, dissolved in 4.5 ml of buffer L (containing: 50 mM Tris-HCl, pH 8.0, 10 mM $MgCl_2$, 10 µM BSA, 25% polyethylene glycol (PEG 8000), 1 mM hexamine cobalt chloride (HCC), 20 µM ATP and 2000 units of T4 RNA ligase (Roche)) is added to the tube containing the beads and incubated for 4 hours at 25° C.

Alternatively, the beads can be resuspended in 1 ml of buffer L containing 0.5 µmol of Oligo #2 and only 400 units of T4 RNA ligase, incubated for 1 hour at 25° C., precipitated to the bottom of the tube and resuspended in a fresh 1 ml aliquot of buffer L containing 0.5 µmol of Oligo #2 and 400 units of T4 RNA ligase. This procedure is performed a total of 5 times.

Another possibility is to resuspend the beads in 1 ml of buffer L containing 2000 units of T4 RNA ligase and 1 mM ddATP, instead of ATP, and performing a single 4 hour-long incubation at 25° C.

Step 9. Denaturation and wash. The beads are pelleted, the contents of the tube are removed and 500 µl of wash buffer W1 is added. Without removing wash buffer W1, 500 µl of denaturation buffer containing 0.1 M NaOH and 300 mM NaCl is added into the tube for 1–2 minutes to denature the nascent polynucleotides and fortuitously hybridized oligonucleotides. The beads are then washed three times with 1 ml of 1×PBS.

Step 10. Capping of 5' phosphate. An aqueous solution of 0.1 M methyl-imidazole pH 7, 0.1 SM EDC, 0.5 M cystamine or another primary amine such as ethylamine or 1-propylamine is added to the beads and incubated for 2 hours at 50° C.

Step 11. Wash. Beads are washed by removing the solution present in the tube, adding 1 ml of wash buffer W1 containing 25 mM Tris-HCl, pH 7.5, 125 mM NaCl and 1 g/L Tween-20®, and removing the wash buffer. This wash is performed twice. A final wash using 1 ml of buffer W2 containing 50 mM Tris-Cl pH 8.2, 10 mM $MgCl_2$, 0.1 mM EDTA, 5 mM dithiothreitol, 0.1 mM spermidine is performed.

Step 12. The nascent polynucleotide is phosphorylated and washed as in steps 4 and 5.

Step 13. After capping and wash (as in steps 6 and 7), the next oligonucleotide (Oligo #n) to be ligated to the nascent polynucleotide is added and incubated as in step 8.

Step 14. Denaturation and wash are performed as in step 9, followed by capping and wash (as in steps 10 and 11). Steps 12 through 14 are repeated as many times as is necessary to assemble the entire polynucleotide. A total of 19 ligation steps are performed to assemble 20 oligonucleotides.

Step 15. Elution. If the linker used in step 1 was cystamine, 2-mercaptoethanol can be used to elute the polynucleotides from the solid support. A 500 µl volume of solution containing 2-mercaptoethanol 0.1 M, dissolved in buffer W1 is added to the beads and incubated for 30 minutes at room temperature. The resulting solution is removed from the beads and transferred to a tube. Ethanol precipitation can be used to partially purify the polynucleotide, and the sample can be stored at −20° C. until needed. Alternatively, a nucleic acid purification kit (Qiaquick purification kit from Qiagen Inc.) can be used to purify and concentrate the polynucleotide.

Step 16. Amplification. An aliquot representing 10 to 50% of the partially purified eluate from step 15 is used as the template for PCR. High-fidelity polymerases such as Pfu (Stratagene), Vent (New England Biolabs, Beverly Mass.) or Pwo (http://www.genaxis.com/) can be used in the PCR according to the manufacturers' recommendations. The resulting PCR product is electrophoresed on an agarose gel to allow the isolation of a useful quantity (>10 ng) of a 1 kb double-stranded DNA molecule. This DNA is cloned using methods known to those skilled in the art by methods described in, for example, Sambrook et al. Alternative uses such as in vitro transcription and translation are possible.

Example 3

5' to 3' Assembly of a 1000 bp Polynucleotide With No Capping

During the incubations described below, the reaction vessel is tumbled end-over-end to keep the beads in suspension.

Step 1. Synthesis. Twenty oligonucleotides, each 50 nucleotides in length are synthesized, deprotected and purified by HPLC according to standard methods. Each oligonucleotide is numbered according to its position in the sequence of the polynucleotide to be synthesized, with the 5'-most oligonucleotide being number 1 and the 3'-most being number 20. Using standard phosphoramidite chemistry, a linker containing a primary amine is attached to the 5'—OH of Oligo #1 (e.g., using TFA Aminolink CE phosphoramidite from Perkin-Elmer, Foster City, Calif.). The linker is attached such that its amine functional group is free to react with the solid support functional groups during the immobilization step (see below). The necessary oligonucleotides can be purchased from a commercial supplier such as Operon Inc., or Sigma Inc. Except for Oligo #1, which should have a primary amine at its 5' end and a free 3' hydroxyl, all oligonucleotides should be synthesized with phosphate groups at their 5' and 3' ends.

Step 2. Immobilization. This step is performed essentially according to the manufacturer's instructions (Pierce Chemical co., Rockford Ill.). For example: in a 1.5 ml microcentrifuge tube, 0.1 µmol of Oligo #1, dissolved in 500 µl conjugation buffer containing 0.1 M MES (N-morpholinoethane sulfonic acid) pH 4.7, 0.9% NaCl, is added to 10 mg of Magnabind carboxyl-derivatized magnetic beads prewashed with 1×PBS containing 100 mM phosphate (pH 7.2) and 150 mM NaCl. Fifty µl of 10 mg/ml EDC (1-ethyl-3-(3-dimethylaminopropyl)carbodiimide) is added to the mixture and incubated for 30 minutes at room temperature (20–25° C.). Unreacted COOH groups on the beads can be quenched with a primary amine such as ethylamine or ethanolamine. The amount of Oligo #1 added to the beads can be varied in order to achieve the coupling of 0.1 µmol of Oligo #1 to the 10 mg of beads.

Step 3. Wash. Unbound oligonucleotides are washed away by removing the solution present in the tube, adding 1 ml of wash buffer W1 containing 25 mM Tris-HCl, pH 7.5, 125 mM NaCl and 1 g/L Tween-20®, and removing the wash buffer. This wash is performed twice. A final wash using ligation buffer L (without ATP and ligase; composition described in step 4) is performed. Finally, the beads are resuspended in 500 µl of buffer L and transferred to a 10 ml conical tube. (The Magnabeads can be conveniently precipitated using a magnetic field according to the manufacturer's instructions.)

Step 4. Ligation. 0.5 µmol of Oligo #2, dissolved in 4.5 ml of buffer L (containing: 50 mM Tris-HCl, pH 8.0, 10 mM MgCl$_2$, 10 µM BSA, 25% polyethylene glycol (PEG 8000), 1 mM hexamine cobalt chloride (HCC), 20 µM ATP and 2000 units of T4 RNA ligase (Roche)) is added to the tube containing the beads and incubated for 4 hours at 25° C.

Alternatively, the beads can be resuspended in 1 ml of buffer L containing 0.5 µmol of Oligo #2 and only 400 units of T4 RNA ligase, incubated for 1 hour at 25° C., precipitated to the bottom of the tube and resuspended in a fresh 1 ml aliquot of buffer L containing 0.5 µmol of Oligo #2 and 400 units of T4 RNA ligase. This procedure is performed a total of 5 times.

Another possibility is to resuspend the beads in 1 ml of buffer L containing 2000 units of T4 RNA ligase and 1 mM ddATP, instead of ATP, and performing a single 4 hour-long incubation at 25° C.

Step 5. Denaturation and wash. The beads are pelleted, the contents of the tube are removed and 500 µl of wash buffer W1 is added. Without removing wash buffer W1, 500 µl of denaturation buffer containing 0.1 M NaOH and 300 mM NaCl is added into the tube for 1–2 minutes to denature the nascent polynucleotides and fortuitously hybridized oligonucleotides. The beads are then washed by removing the solution present in the tube, adding 1 ml of wash buffer X containing 0.25 M Tris-HCl, pH 7.5, 0.125 M NaCl, 2 mM MgCl$_2$ and 3 g/l Tween-20®, and removing the wash buffer. This wash is performed twice. A final wash with 1 ml of phosphatase buffer (100 mM NaCl, 50 mM Tris-HCl, 10 mM MgCl$_2$, 1 mM dithiothreitol (pH 7.9 at 25° C.)) is performed.

Step 6. Deprotection. The 3' phosphates of the nascent polynucleotides are removed by adding to the beads 1000 units of calf intestinal phosphatase (New England Biolabs, Beverly, Mass.) diluted in 1 ml of phosphatase buffer containing 100 mM NaCl, 50 mM Tris-HCl, 10 mM MgCl$_2$, 1 mM dithiothreitol (pH 7.9 at 25° C.).

Step 7. Phosphatase inactivation. The beads are washed twice with a solution containing 10 mM Tris pH8 and 5 mM EDTA. Any remaining phosphatase is then inactivated by heating the beads to 75° C. for 10 minutes in 1 ml of 5 mM EDTA (pH 8.0).

Step 8. Steps 3 to 7 are repeated as many times as is necessary to assemble the entire polynucleotide. A total of 19 ligation steps are performed to assemble 20 oligonucleotides.

Step 9: After washing the beads, and the polynucleotide attached to them, three times with water and once with PCR buffer (typically supplied by manufacturers of thermostable polymerases) an aliquot representing 10 to 50% of the magnabeads is added directly to a PCR mixture. High-fidelity polymerases such as Pfu (Stratagene), Vent (New England Biolabs, Beverly Mass.) or Pwo (www.genaxis.com) can be used in the PCR according to the manufacturers' recommendations. The resulting PCR product is electrophoresed on an agarose gel to allow the isolation of a useful quantity (>10 ng) of a 1 kb double-stranded DNA molecule. This DNA is cloned using methods known to those skilled in the art. Alternative uses of the polynucleotide or its amplification product, such as templates for in vitro transcription and in vitro translation, are also possible.

Example 4

5' to 3' Assembly of a 1000 bp Polynucleotide With Capping

During the incubations described below, the reaction vessel is tumbled end-over-end to keep the beads in suspension.

Step 1. Synthesis. Twenty oligonucleotides, each 50 nucleotides in length are synthesized, deprotected and purified by HPLC according to standard methods. Each oligonucleotide is numbered according to its position in the sequence of the polynucleotide to be synthesized, with the 5'-most oligonucleotide being number 1 and the 3'-most being number 20. Using standard phosphoramidite chemistry, a linker containing a primary amine is attached to the 5'—OH of Oligo #1 (e.g., using TFA Aminolink CE phosphoramidite from Perkin-Elmer, Foster City, Calif.). The linker is attached such that its amine functional group is free to react with the solid support functional groups during the immobilization step (see below). The necessary oligonucleotides can be purchased from a commercial supplier such as Operon Inc., or Sigma Inc. Except for Oligo #1, which should have a primary amine at its 5' end and a free 3' hydroxyl, all oligonucleotides should be synthesized with phosphate groups at their 5' and 3' ends.

Step 2. Immobilization. This step is performed essentially according to the manufacturer's instructions (Pierce Chemical co., Rockford Ill.). For example: in a 1.5 ml microcentrifuge tube, 0.1 μmol of Oligo #1, dissolved in 500 μl conjugation buffer containing 0.1 M MES (N-morpholinoethane sulfonic acid) pH 4.7, 0.9% NaCl, is added to 10 mg of Magnabind carboxyl-derivatized magnetic beads prewashed with 1×PBS containing 100 mM phosphate (pH 7.2) and 150 mM NaCl. Fifty μl of 10 mg/ml EDC (1-ethyl-3-(3-dimethylaminopropyl)carbodiimide) is added to the mixture and incubated for 30 minutes at room temperature (20–25° C.). Unreacted COOH groups on the beads can be quenched with a primary amine such as ethylamine or ethanolamine. The amount of Oligo #1 added to the beads can be varied in order to achieve the coupling of 0.1 μmol of Oligo #1 to the 10 mg of beads.

Step 3. Wash. Unbound oligonucleotides are washed away by removing the solution present in the tube, adding 1 ml of wash buffer W1 containing 25 mM Tris-HCl, pH 7.5, 125 mM NaCl and 1 g/L Tween-20®, and removing the wash buffer. This wash is performed twice. A final wash using ligation buffer L (minus the ATP and ligase; composition described in step 4) is performed. Finally, the beads are resuspended in 500 μl of buffer L and transferred to a 10 ml conical tube. (The Magnabeads can be conveniently precipitated using a magnetic field according to the manufacturer's instructions.)

Step 4. Ligation. 0.5 μmol of Oligo 42, dissolved in 4.5 ml of buffer L (containing: 50 mM Tris-HCl, pH 8.0, 10 mM MgCl$_2$, 10 μM BSA, 25% polyethylene glycol (PEG 8000), 1 mM hexamine cobalt chloride (HCC), 20 μM ATP and 2000 units of T4 RNA ligase (Roche)) is added to the tube containing the beads and incubated for 4 hours at 25° C.

Alternatively, the beads can be resuspended in 1 ml of buffer L containing 0.5 μmol of Oligo #2 and only 400 units of T4 RNA ligase, incubated for 1 hour at 25° C., precipitated to the bottom of the tube and resuspended in a fresh 1 ml aliquot of buffer L containing 0.5 μmol of Oligo #2 and 400 units of T4 RNA ligase. This procedure is performed a total of 5 times.

Another possibility is to resuspend the beads in 1 ml of buffer L containing 2000 units of T4 RNA ligase and 1 mM ddATP, instead of ATP, and performing a single 4 hour-long incubation at 25° C.

Step 5. Denaturation and wash. The beads are pelleted, the contents of the tube are removed and 500 μl of wash buffer W1 is added. Without removing wash buffer W1, 500 μl of denaturation buffer containing 0.1 M NaOH and 300 mM NaCl is added into the tube for 1–2 minutes to denature the nascent polynucleotides and fortuitously hybridized oligonucleotides. The beads are then washed twice with 1 ml of 1×PBS, and twice with 1 ml of dry DMF (dimethyl formamide).

Step 6. Capping of non-phosphorylated 3' OH. The beads are resuspended in 1 ml of DMF containing 100 μmol (11 μl) of isopropenyl acetate and 1 mg of subtilisin 8350 and incubated up to 24 hours at 45° C.

Step 7. Wash. Beads are washed twice with DMF, twice with wash buffer W1 containing 25 mM Tris-HCl, pH 7.5, 125 mM NaCl and 1 g/L Tween-20®, and once with phosphatase buffer (100 mM NaCl, 50 mM Tris-HCl, 10 mM MgCl$_2$, 1 mM dithiothreitol, pH 7.9 at 25° C.)].

Step 8. Deprotection. The 3' phosphates of the nascent polynucleotides are removed by adding to the beads 1000 units of calf intestinal phosphatase (New England Biolabs, Beverly, Mass.) diluted in 1 ml of phosphatase buffer containing 100 mM NaCl, 50 mM Tris-HCl, 10 mM MgCl$_2$, 1 mM dithiothreitol (pH 7.9 at 25° C.).

Step 9. Phosphatase inactivation. The beads are washed twice with a solution containing 10 mM Tris pH8 and 5 mM EDTA. Any remaining phosphatase is then inactivated by heating the beads to 75° C. for 10 minutes in 1 ml of 5 mM EDTA (pH 8.0).

Step 10. Steps 3 to 9 are repeated as many times as is necessary to assemble the entire polynucleotide. A total of 19 ligation steps are performed to assemble 20 oligonucleotides.

Step 11. After washing the beads, and the polynucleotide attached to them, three times with water and once with PCR buffer (typically supplied by manufacturers of thermostable polymerases) an aliquot representing 10 to 50% of the magnabeads is added for PCR. High-fidelity polymerases such as Pfu (Stratagene), Vent (New England Biolabs, Beverly Mass.) or Pwo (http://www.genaxis.com/) can be used in the PCR according to the manufacturers' recommendations. The resulting PCR product is electrophoresed on an agarose gel to allow the isolation of a useful quantity (>10 ng) of a 1 kb double-stranded DNA molecule. This DNA is cloned using methods known to those skilled in the art. Alternative uses of the polynucleotide or its amplification product such as templates for in vitro transcription and in vitro translation are also possible.

Example 5

Directed Evolution of T4 RNA Ligase (g63)

First, g63 is subcloned by PCR into a convenient expression vector such as pBADmyc/hisA (Invitrogen, Carlsbad, Calif.) using a publicly available gene as a template (ATCC, Manassas, Va.) and appropriate primers. Specifically, primers sph1 (5' GCGAAGCGG CATGCATAATG; SEQ ID NO:1) and badmcs_xho_ant (5' GTTCTTGCATCTC-GAGATTCC TCCTGTTAGCCCAAAAAACG; SEQ ID NO:2) are used to amplify via PCR a fragment of plasmid pBADmyc/hisA (Invitrogen, Carlsbad, Calif.). Primers T4_xho_sns (5'GGAATCTCGAGATGCAAGAACTT TTTAACAATTTAATGG; SEQ ID NO:3) and T4_Hindant (5' CGAGGGACTTGTAAAGCTTCTAGTATC-CTTCTGGG; SEQ ID NO:4) are used to amplify g63 by PCR. All primers are synthesized by Operon (Alameda, Calif.). The two PCR products are fused into a single DNA fragment via overlap PCR. Briefly, a standard PCR reaction is performed wherein the two PCR products described above are mixed together as templates in roughly equimolar amounts along with two primers (sph1 and T4_Hind_ant). The PCR reaction is allowed to proceed normally to yield a DNA fragment that is then cloned into pBADmyc/hisA by restriction digestion and ligation according to well established methods using SphI and HindIII restriction sites both present in the PCR product and plasmid. The resulting construct is called pBADg63.

A population of mutant g63 genes (mutant library) is then constructed, for example by error-prone PCR. The g63 gene is amplified via error-prone PCR using oligonucleotides which introduce appropriate unique restriction sites at the 5' and 3' ends of the gene (e.g., T4_xho_sns and T4_Hind_ ant). The resulting PCR product is a population of mutated g63 genes that can be cloned, using standard methods into plasmid pBADg63 via XhoI and HindIII restriction sites present in both PCR product and plasmid. The library thus obtained is then screened for RNA ligase variants with improved activity.

Since most variants will be similar to or less active than wild-type (wt), a screen that can evaluate thousands of clones in a few days is preferred. This can be achieved, for example, by a robotic system which picks individual bacterial colonies, grows them in 96-well plates containing a growth medium such as LB supplemented with carbenicillin (60 µg/ml) and L-arabinose at a concentration of 0.002% to 0.2% (wt/vol). The cultures are grown at 30 to 37° C. for 12 to 24 hours to express useful amounts of RNA ligase, wt or variant. A lysis agent such as B-PER (Pierce, Ill.) is added by a robot to the grown cultures to release the expressed RNA ligase from the bacterial cells (i.e., lyse the cells). An aliquot of each lysate is transferred robotically from a well of a growth plate to a well of a corresponding 96-well assay plate containing reagents that will allow automated monitoring of the reaction catalyzed by RNA ligase variants.

To evolve an RNA ligase that efficiently ligates oligonucleotides, each mutant must be screened for this activity. The reagents of the assay plate therefore include a donor and an acceptor oligonucleotide (1 µM each), 50 mM Tris-Cl, pH 8.0, 10 mM $MgCl_2$, 10 µM BSA, 25% polyethylene glycol (PEG 8000), 1 mM hexamine cobalt chloride (HCC), 20 µM ATP and a molecular beacon that specifically recognizes the ligation product of the donor and acceptor oligonucleotides. As the RNA ligase variant catalyzes the ligation of the donor and acceptor oligonucleotides, molecular beacon molecules will emit a fluorescence signal that increases with time. Assay plate wells in which fluorescence increases more rapidly than control wells containing wild type RNA ligase indicate the presence of a variant with improved activity.

The entire disclosure of each publication cited herein is hereby incorporated by reference.

What is claimed is:

1. A method of preparing a polynucleotide having at least 200 nucleotides and a predetermined nucleotide sequence comprising the steps:
   a) providing a solid support;
   b) providing a plurality of oligonucleotides, wherein the combination of the nucleotide sequences of said oligonucleotides comprises the nucleotide sequence of said polynucleotide;
   c) contacting said solid support with the 3' terminus of a first oligonucleotide from said plurality of oligonucleotides to form a tethered oligonucleotide;
   d) ligating the 3' terminus of another oligonucleotide from said plurality of oligonucleotides to the 5' terminus of said tethered oligonucleotide, wherein said ligating is carried out in the presence of RNA ligase or ribozyme;
   e) phosphorylating the 5' terminus of said another oligonucleotide; and
   f) repeating steps d) and e) until said polynucleotide is prepared.

2. The method of claim 1 wherein said solid support is selected from the group consisting of agarose, polyacrylamide, magnetic beads, polystyrene, polyacrylate, controlled-pore glass, hydroxyethylmethacrylate, polyamide, polyethylene, polyethyleneoxy, and polyethyleneoxy/polystyrene copolymer.

3. The method of claim 1 wherein the 5' terminus of said first oligonucleotide is phosphorylated prior to contacting said solid support with said first oligonucleotide.

4. The method of claim 3 wherein said phosphorylation is carried out with a phosphoramidite or kinase.

5. The method of claim 1 wherein said 5' terminus of said tethered oligonucleotide is phosphorylated after contacting said solid support with said first oligonucleotide.

6. The method of claim 5 wherein said phosphorylation is carried out with a phosphoramidite or kinase.

7. The method of claim 1 wherein prior to ligation of said tethered oligonucleotide to said another of said plurality of oligonucleotides, any tethered oligonucleotide with an unphosphorylated 5' terminus is capped.

8. A method of preparing a polynucleotide having at least 200 nucleotides and a predetermined nucleotide sequence comprising the steps:
   a) providing a solid support;
   b) providing a plurality of oligonucleotides, wherein the combination of the nucleotide sequences of said oligonucleotides comprises the nucleotide sequence of said polynucleotide;
   c) contacting said solid support with the 3' terminus of a first oligonucleotide from said plurality of oligonucleotides to form a tethered oligonucleotide;
   d) ligating the 3' terminus of another oligonucleotide from said plurality of oligonucleotides to the 5' terminus of said tethered oligonucleotide; and
   e) repeating step d) until said polynucleotide is prepared, wherein prior to ligation of said tethered oligonucleotide to said another of said plurality of oligonucleotides, any tethered oligonucleotide with an unphosphorylated 5' terminus is capped, and wherein said capping is carried out with an enzyme which oxidizes said 5'—OH terminus of said unphosphorylated tethered oligonucleotide.

9. The method of claim 8 wherein enzyme is a nucleoside oxidase.

10. A method of preparing a polynucleotide having at least 200 nucleotides and a predetermined nucleotide sequence comprising the steps:
   a) providing a solid support;
   b) providing a plurality of oligonucleotides, wherein the combination of the nucleotide sequences of said oligonucleotides comprises the nucleotide sequence of said polynucleotide;
   c) contacting said solid support with the 3' terminus of a first oligonucleotide from said plurality of oligonucleotides to form a tethered oligonucleotide;
   d) ligating the 3' terminus of another oligonucleotide from said plurality of oligonucleotides to the 5' terminus of said tethered oligonucleotide; and
   e) repeating step d) until said polynucleotide is prepared, wherein prior to ligation of said tethered oligonucleotide to said another of said plurality of oligonucleotides, any tethered oligonucleotide with an unphosphorylated 5' terminus is capped, and wherein said capping is carried out with an enzyme which acylates said 5'—OH terminus of said unphosphorylated tethered oligonucleotide.

11. The method of claim 10 wherein said enzyme is lipase or subtilisin.

12. The method of claim 1 wherein said RNA ligase is T4 RNA ligase or modified T4 RNA ligase.

13. The method of claim 1 wherein the 5' terminus of said another of said plurality of oligonucleotides is phosphorylated prior to ligation to said tethered oligonucleotide.

14. The method of claim 1 wherein the 5' terminus of said another of said plurality of oligonucleotides is not phosphorylated prior to ligation of said tethered oligonucleotide to said another of said plurality of oligonucleotides, and wherein after said ligation the 5' terminus of any of said tethered oligonucleotide that remains unligated is capped.

15. The method of claim 14 wherein said capping is care out by forming a phosphamide or reaction with a blocking oligonucleotide.

16. The method of claim 15 wherein said blocking oligonucleotide is a 5'deoxyoligonucleotide or an oligonucleotide comprising a 5' fluorescent label.

17. The method of claim 1 wherein said polynucleotide is selected from the group consisting of a gene, plasmid, viroid, or a polynucleotide comprising an origin of replication.

18. The method of claim 1, wherein a plurality of polynucleotides are simultaneously prepared on said solid support.

19. The method of claim 1 wherein said plurality of polynucleotides are degenerate polynucleotides.

20. A method of preparing a polynucleotide having at least 200 nucleotides and a predetermined nucleotide sequence comprising the steps:
   a) providing a solid support;
   b) providing a plurality of oligonucleotides, wherein the combination of the nucleotide sequences of said oligonucleotides comprises the nucleotide sequence of said polynucleotide;
   c) contacting said solid support with the 5' terminus of a first oligonucleotide from said plurality of oligonucleotides to form a tethered oligonucleotide;
   d) ligating the 5' terminus of another oligonucleotide from said plurality of oligonucleotides to the 3' terminus of said tethered oligonucleotide, wherein the 3' OH terminus of said another oligonucleotide is blocked by acylation; and
   e) repeating step d) until said polynucleotide is prepared.

21. The method of claim 20 wherein said solid support is selected from the group consisting of agarose, polyacrylamide, magnetic beads, polystyrene, polyacrylate, controlled-pore glass, hydroxyethylmethacrylate, polyamide, polyethylene, polyethyleneoxy, and polyethyleneoxy/polystyrene copolymer.

22. The method of claim 20 wherein said 5' terminus of said another oligonucleotide from said plurality of oligonucleotides is phosphorylated.

23. The method of claim 22 wherein said phosphorylation is carried out with a phosphoramidite or kinase.

24. The method of claim 20 wherein said ligating step is carried out with a RNA ligase or ribozyme.

25. The method of claim 24 wherein said RNA ligase is T4 RNA ligase or modified T4 RNA ligase.

26. The method of claim 20 wherein after said ligation of said another oligonucleotide to said tethered oligonucleotide, said 3' terminus of any unligated tethered oligonucleotide is capped.

27. The method of claim 26 wherein said capping is carried out with an enzyme which acylates said 3'—OH terminus of said unligated tethered oligonucleotide.

28. The method of claim 27 wherein said enzyme is a lipase or subtilisin.

29. The method of claim 26 wherein said capping is carried out with an enzyme which adds at least one dideoxy nucleotide to said 3' terminus of said unligated tethered oligonucleotide.

30. The method of claim 29 wherein said enzyme is terminal transferase.

31. The method of claim 20 wherein after ligation of said tethered oligonucleotide to said another oligonucleotide having a blocked 3' terminus, said blocked 3' terminus is deblocked.

32. The method of claim 31 wherein said deblocking of said blocked 3' terminus of said tethered oligonucleotide is carried out by using a subtilisin or a lipase.

33. The method of claim 20, wherein said polynucleotide is selected from the group consisting of a gene, plasmid, viroid, or a polynucleotide comprising an origin of replication.

34. The method of claim 20, wherein a plurality of polynucleotides are simultaneously prepared on said solid support.

35. The method of claim 20 wherein said plurality of polynucleotides are degenerate polynucleotides.

* * * * *

UNITED STATES PATENT AND TRADEMARK OFFICE
CERTIFICATE OF CORRECTION

PATENT NO.    : 6,479,262 B1
DATED         : November 12, 2002
INVENTOR(S)   : Simon Delagrave It is certified that error appears in the above-identified patent and that said Letters Patent is hereby corrected as shown below:

<u>Title page,</u>
Item [56], References Cited, OTHER PUBLICATIONS, "Harada K., et al.," reference, please delete "selectiion" and insert -- selection -- therefor.

<u>Column 3,</u>
Line 62, please delete "2O-methylcytidine" and insert -- 2-O-methylcytidine -- therefor.

<u>Column 17,</u>
Line 26, please delete "Oligo 42" and insert -- Oligo #2 -- therefor.

<u>Column 22,</u>
Line 32, please delete "care" and insert -- carried -- therefor.

Signed and Sealed this

Fourth Day of January, 2005

JON W. DUDAS
*Director of the United States Patent and Trademark Office*

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Primer Oligonucleotide

<400> SEQUENCE: 1
gcgaagcggc atgcataatg                                                           20

<210> SEQ ID NO 2
<211> LENGTH: 41
<212> TYPE: DNA
<213> ORGANISM: Artificial Sequence
<220> FEATURE:
<223> OTHER INFORMATION: Primer Oligonucleotide

<400> SEQUENCE: 2
gttcttgcat ctcgagattc ctcctgttag cccaaaaaac g                                   41

<210> SEQ ID NO 3
<211> LENGTH: 39
<212> TYPE: DNA
<213> ORGANISM: Artificial Sequence
<220> FEATURE:
<223> OTHER INFORMATION: Primer Oligonucleotide

<400> SEQUENCE: 3
ggaatctcga gatgcaagaa cttttttaaca atttaatgg                                     39

<210> SEQ ID NO 4
<211> LENGTH: 35
<212> TYPE: DNA
<213> ORGANISM: Artificial Sequence
<220> FEATURE:
<223> OTHER INFORMATION: Primer Oligonucleotide

<400> SEQUENCE: 4
cgagggactt gtaaagcttc tagtatcctt ctggg                                          35